(12) United States Patent
Hein et al.

(10) Patent No.: US 8,394,117 B2
(45) Date of Patent: Mar. 12, 2013

(54) HANDHELD APPARATUS FOR CREATING A PUNCTURE WOUND

(75) Inventors: Heinz-Michael Hein, Udligenswil (CH); Irio Calasso, Arth (CH); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 470 days.

(21) Appl. No.: 12/040,905

(22) Filed: Mar. 2, 2008

(65) Prior Publication Data

US 2008/0208079 A1    Aug. 28, 2008

Related U.S. Application Data

(63) Continuation of application No. PCT/EP2006/007779, filed on Aug. 5, 2006.

(30) Foreign Application Priority Data

Sep. 3, 2005  (EP) .................................. 05019190

(51) Int. Cl.
*A61B 17/14* (2006.01)
*A61B 17/32* (2006.01)
*A61B 17/34* (2006.01)
*B26F 1/24* (2006.01)

(52) U.S. Cl. .............................. 606/181; 83/30; 606/185

(58) Field of Classification Search .................. 600/583, 600/584; 606/181–183, 184–189, 171, 177; 83/584, 30
See application file for complete search history.

(56) References Cited

U.S. PATENT DOCUMENTS

| | | | | |
|---|---|---|---|---|
| 2,424,138 A * | 7/1947 | Barr | ................................. | 60/379 |
| 4,469,110 A | 9/1984 | Slama | | |
| 5,370,654 A * | 12/1994 | Abidin et al. | .................. | 606/182 |
| 6,364,889 B1 | 4/2002 | Kheiri et al. | | |
| 6,409,740 B1 * | 6/2002 | Kuhr et al. | ..................... | 606/182 |
| 6,589,260 B1 | 7/2003 | Redeker et al. | | |
| 6,743,211 B1 | 6/2004 | Prausnitz et al. | | |
| 6,884,252 B1 * | 4/2005 | Urich et al. | ..................... | 606/166 |
| 7,223,276 B2 | 5/2007 | List et al. | | |
| 2001/0039058 A1 * | 11/2001 | Iheme et al. | .................. | 436/180 |
| 2002/0082522 A1 | 6/2002 | Douglas et al. | | |
| 2004/0092996 A1 * | 5/2004 | List et al. | ...................... | 606/181 |
| 2006/0036187 A1 * | 2/2006 | Vos et al. | ...................... | 600/576 |

FOREIGN PATENT DOCUMENTS

| | | |
|---|---|---|
| EP | 1 090 584 | 4/2001 |
| EP | 1 101 443 | 5/2001 |
| EP | 1 384 438 | 1/2004 |
| WO | WO 01/89383 | 11/2001 |
| WO | WO 03/088824 | 10/2003 |
| WO | WO 2004/041087 | 5/2004 |
| WO | WO 2005/104949 | 11/2005 |

* cited by examiner

*Primary Examiner* — Max Hindenburg
*Assistant Examiner* — John Pani
(74) *Attorney, Agent, or Firm* — Bose McKinney & Evans LLP

(57) ABSTRACT

The invention relates to a method for creating a puncture wound for obtaining a sample of a body fluid from a body part in which a skin opening is created at a puncture site in the epidermis in a skin-opening step. Then, in a sample collection step a sample collection puncture is executed by using a puncture element with which the skin opening is deepened with the puncture element, thereby creating a puncture wound for obtaining the sample. The invention also relates to a handheld apparatus for implementing this method.

18 Claims, 6 Drawing Sheets

HANDHELD APPARATUS FOR CREATING A PUNCTURE WOUND

RELATED APPLICATIONS

This application is a continuation application of International Application PCT/EP2006/007779, filed Aug. 5, 2006, which claims priority to EP 05 019 190.7, filed Sep. 3, 2005, which are hereby incorporated by reference in their entirety.

BACKGROUND

The invention relates to a method for creating a puncture wound for obtaining a sample of body fluid from a body part and to a suitable handheld apparatus, comprising a puncture element, a drive by which the puncture element is movable in a direction towards the skin and in a direction away from the skin, and a control unit for controlling the movement of the puncture element.

For withdrawing a small amount of blood or interstitial fluid from a body part, e.g., a finger, for analytical diagnostic purposes, puncture elements, e.g., needles or lancets, are used to puncture the corresponding body part, thereby generating a puncture wound. Specially trained personnel are required when this is done manually. Nevertheless, such a puncture is still associated with considerable pain.

Blood-sampling systems comprising a puncture device and the respective lancets adapted specifically to the particular device have been in use for a long time. A housing of the puncture device holds a drive capable of moving the puncture element in the direction towards the skin and in the direction away from the skin. A spring is used as the drive element for the puncture movement. Early in the development of such devices, very simple designs were customary in which the lancet was attached directly to one end of a compression spring arranged in an elongated housing (e.g., U.S. Pat. No. 4,469,110).

However, such blood-sampling systems do not fulfill the high demands that must be met when regular monitoring of analytical blood values is required. This is particularly true for diabetics, who should monitor their blood sugar level frequently to be able to keep it within certain limits by means of insulin injection or dietary controls. Extensive scientific study has shown that a dramatic reduction in extremely severe late consequences of diabetes mellitus (e.g., retinopathy with the resulting blinding of the patient) can be achieved by intensive therapy with at least four blood tests per day.

This intensive therapy requires that generation of the blood sample causes the least possible pain. Numerous different blood-sampling systems have been developed with the goal of achieving an improvement in this regard.

To achieve blood sampling with the least possible pain it is considered essential that the puncture-and-return movement of the puncture element should be as fast as possible, without vibration and with an optimal puncture depth. An optimal puncture depth is considered here to be a depth no greater than that which is absolutely necessary to reach blood-carrying layers of tissue.

A handheld apparatus of the type described in US 2004/0092996 allows relatively painless blood sampling. In such a handheld apparatus, the drive comprises a drive spring for creating a drive force and a drive rotor that executes a rotational movement driven by the drive force. Rotational movements of the drive rotor are converted into a puncture-and-return movement of the puncture element by a control unit comprising a curve control linked to the drive rotor.

Furthermore, electric puncture devices are known, for example, from U.S. Pat. No. 6,364,889. Here a puncture-and-return movement of the lancet is driven by the magnetic force of a coil. Electric puncture devices have the advantage that the speed of the puncture element can be controlled with high precision. WO 03/088824 recommends in this regard that in a puncture movement the stratum corneum be punctured at a maximum speed and that the lancet then be decelerated, so that penetration into deeper layers of the skin takes place at a lower speed. Such a puncture movement, in which the lancet speed is reduced with the depth of penetration, aims to reduce painful pressure waves.

Despite the extensive development work that has led to the designs mentioned above and numerous other constructions, there still remains great interest in sample collection systems and methods which fulfill as far as possible the difficult and sometimes contradictory requirements (minimal pain perception, reliable collection of a sufficient quantity of sample, simple operability, compact design, inexpensive construction) simultaneously.

SUMMARY OF THE INVENTION

The present invention provides a method by which a puncture wound for collecting a sample of body fluid from a body part can be produced with less pain. This is achieved in exemplary embodiments by a method for producing a puncture wound for collecting a sample of body fluid from a body part in which method a skin opening is created at a puncture site in the epidermis in a skin-opening step. A sample collection puncture is then executed in a sample collection step by means of a puncture element, wherein the depth of the skin opening is increased with the puncture element, thus producing a puncture wound for collecting the sample.

In exemplary embodiments, this method is carried out with a handheld apparatus for creating a puncture wound, the apparatus comprising a puncture element, a drive for moving the puncture element in the direction towards the skin and in the direction away from the skin and a control unit for controlling the movement of the puncture element. The apparatus has a means by which an opening in the skin is created in the epidermis at a puncture site in a skin-opening step and the control unit is adapted for performing, after the skin-opening step, a sample collection puncture by means of a puncture element, and a sample collection step, in which the depth of the skin opening is increased with the puncture element and thus a puncture wound for collecting the sample is created. The handheld apparatus is adapted in particular for performing the exemplary method, and to this end, it contains means for automatically performing the process steps thereof.

According to the prior art, a puncture wound is produced in a single step with a puncture-and-reverse movement. According to these teachings, two separate steps are performed, namely, first, a skin-opening step in which a skin opening is created at a puncture site in the epidermis, and then a sample collection step in which a sample collection puncture is performed by means of a puncture element, thereby increasing the depth of the skin opening and thereby creating a puncture wound.

An essential basis of these teachings is the finding that with a traditional puncture-and-return movement, the puncture element is decelerated in its forward movement due to friction in the upper layers of skin, in particular, the stratum corneum, before reaching deeper layers of tissue that deliver blood. This results in a pressure wave, which starts from the friction surfaces of the lancet, propagates through the tissue, and causes pain. The occurrence of a painful pressure wave can be prevented by first creating, in a skin opening step, a skin opening at a puncture site in the epidermis, the depth of this skin opening being so small that it causes practically no pain. The stratum corneum and deeper layers of the epidermis can relax within a very short period of time, so that in a subsequent sample collection step, e.g., 1 msec after the end of the skin-opening step, the skin opening can be deepened and a puncture wound can be created for collecting the sample. Again, the pain is less than with known methods. With an optimal setting of the puncture parameters, the pain is only insignificantly greater than in the skin-opening step, so that on the whole a largely pain-free collection of blood is achieved. When the sample collection puncture takes place, a skin opening is already present. Therefore, the friction that occurs is so small that the painful pressure wave is avoided.

The skin-opening step may be separated from the sample collection step, for example, by using a different means than the puncture element for the skin opening. For example, a laser could be used, which creates a brief laser light pulse for vaporizing, at the puncture site, a portion of the epidermis, e.g., a large portion of the stratum corneum. In other embodiments, however, the same puncture element used for the sample collection step is also used for the skin-opening step. The sample collection step can be separated from the skin-opening step by the fact that the puncture element is decelerated at the end of the skin-opening step, preferably stopped, and accelerated again for the sample collection step. If the puncture element moves after the deceleration only slowly or not at all in the puncture direction, the epidermis can relax before the depth of the skin opening is increased in the sample collection step.

The depth of the puncture can be adjusted and controlled much more precisely according to these teachings than with methods according to the prior art. With a traditional puncture-and-return movement, friction forces lead to a considerable deformation of the skin surface. In puncturing the stratum corneum, an indentation (dimple) is formed in the skin at the puncture site, so that the lancet actually penetrates to a lesser depth beneath the deformed skin surface, than would be expected on the basis of the lancet stroke when the device is in contact with the skin surface.

The distance by which the epidermis and blood-carrying layers of tissue are deformed by the puncture element due to this effect depends on the kinetics of the puncture movement, the shape of the puncture element, and also on the elastic properties of the patient's skin at the point in time of the puncture at the puncture site. If a skin opening is first created in the epidermis at the puncture site in a skin-opening step before the sample collection step, the effect of the indentation of the skin at the puncture site is significantly reduced, such that the puncture depth can be controlled and adjusted much more precisely. These teachings therefore allow creating a puncture only as deep as is necessary to obtain the sample.

The skin opening created in the skin-opening step is preferably located entirely in the stratum corneum. However, it is acceptable if the puncture element in the skin-opening step also penetrates into a deeper layer of the epidermis, i.e., the stratum lucidum, stratum granulosum, stratum spinosum or even into the stratum basale, because these layers do not contain nerves or blood vessels. At any rate, blood-carrying tissue should only be reached in the sample collection step. A practically painless skin-opening step can be achieved if the skin opening created in the skin-opening step has a depth of between 0.8 mm and can be 1.2 mm.

The puncture element is preferably stopped and retracted after the skin-opening step. In exemplary embodiments, it is withdrawn completely out of the epidermis so that the sample collection step includes a new puncture movement, i.e., a sample collection puncture. However, as already mentioned, it is in principle sufficient if the puncture element is decelerated to a sufficient degree and for a sufficient period of time at the end of the skin-opening step that the epidermis at or surrounding the skin opening can relax before the puncture element is again accelerated and the skin opening is deepened by advancing the puncture element to create the puncture wound. The retraction, in particular, complete retraction, makes it possible to accelerate the puncture element to a higher speed before it penetrates into blood-carrying layers of tissue, so that the sample collection puncture can be performed with higher speed and thus especially little pain. Furthermore, frictional forces occurring during the retraction of the puncture element support the relaxation process, so that the sample collection puncture can be performed immediately after complete withdrawal of the puncture element out of the skin.

In a different context, it is known from WO 2004/041087 that punctures may be made twice in succession into the same puncture site using one puncture element. In contrast to these teachings, however, with the known device, a blood-carrying layer of tissue is reached with the first puncture. The second puncture is made to a lesser depth. According to these teachings, the contrary geometric relationship applies because with the second puncture, namely, the sample collection puncture, a greater depth is reached than in the first puncture, the skin-opening puncture. The known method also does not have the goal of reducing the pain associated with the sample collection. Its goal is to instead increase the amount of blood obtained from the puncture wound. The second puncture serves to prevent premature closing of the puncture wound so that blood is conveyed out of the puncture wound through a capillary gap created by the puncture element. This finding from WO 2004/041087 can be utilized in the present invention by a third puncture, which has a lesser depth of puncture than the sample collection puncture.

Embodiments of the present invention are explained in greater detail below with reference to the accompanying drawings. Exemplary embodiments of handheld devices for performing the described method are illustrated. The same or corresponding components are labeled with the same reference numerals in the drawings.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
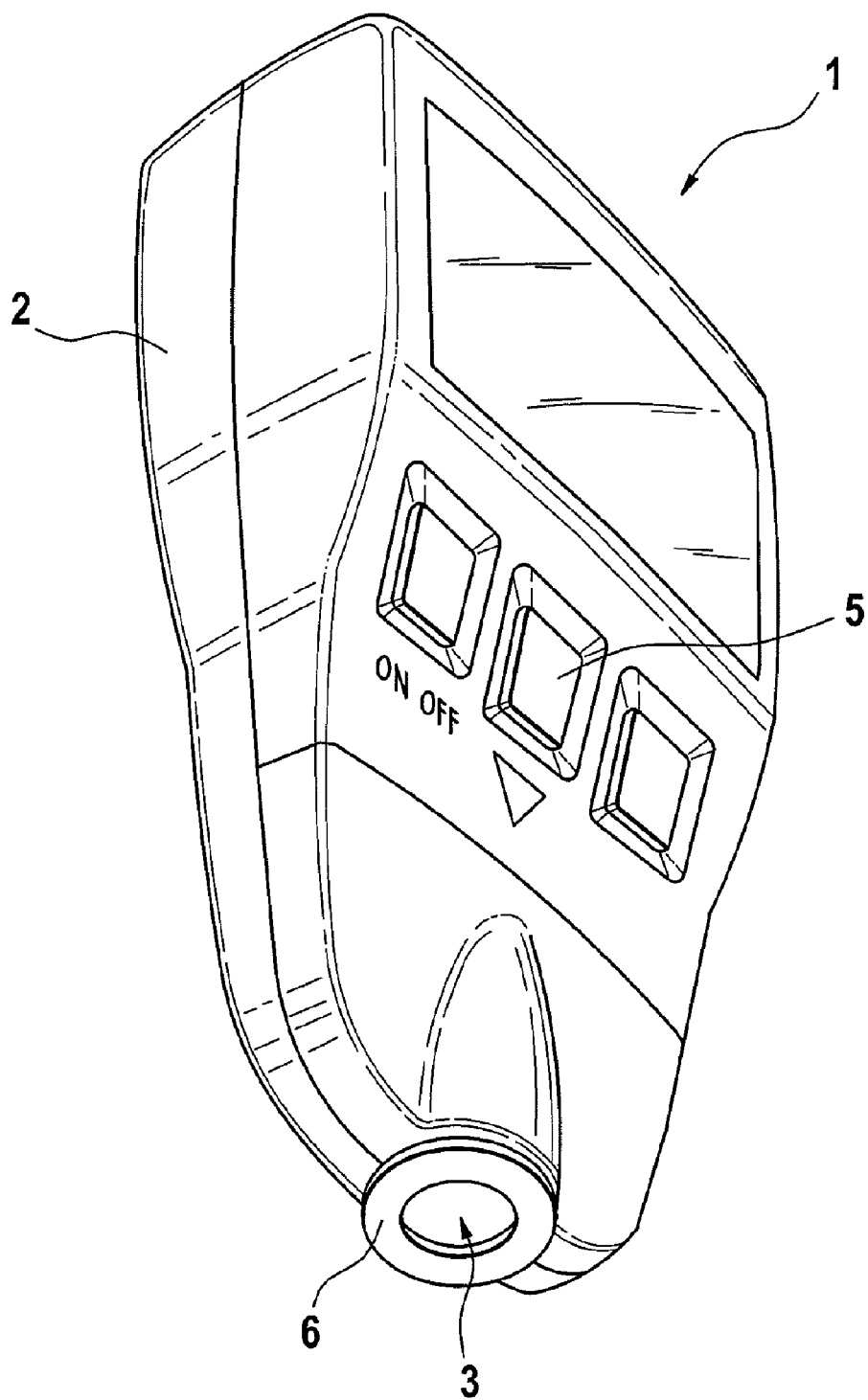
FIG. 1 is a perspective view of a handheld apparatus according to an embodiment of the present invention.

The handheld apparatus 1 shown in FIG. 1 serves to create a puncture wound for withdrawing body fluid, in particular blood and/or interstitial fluid for diagnostic purposes. The housing 2 has a housing opening 3 for placing against a finger and has an operating means in the form of buttons 5.

To promote circulation in the tissue at the puncture site, the housing opening 3 may be surrounded by a pressure ring 6 which undergoes elastic deformation when it is pressed against a body part. For example, the pressure ring 6 may be made of a rubber elastic plastic. The pressure ring 6 preferably has a pressure surface that is inclined inward and on which a finger or other body part is placed during use. A suitable pressure ring is described in detail in U.S. Pat. No. 6,589,260, which is incorporated herein by reference. In U.S. Pat. No. 6,589,260 the pressure ring is designated as "compression unit."

Figure 2:
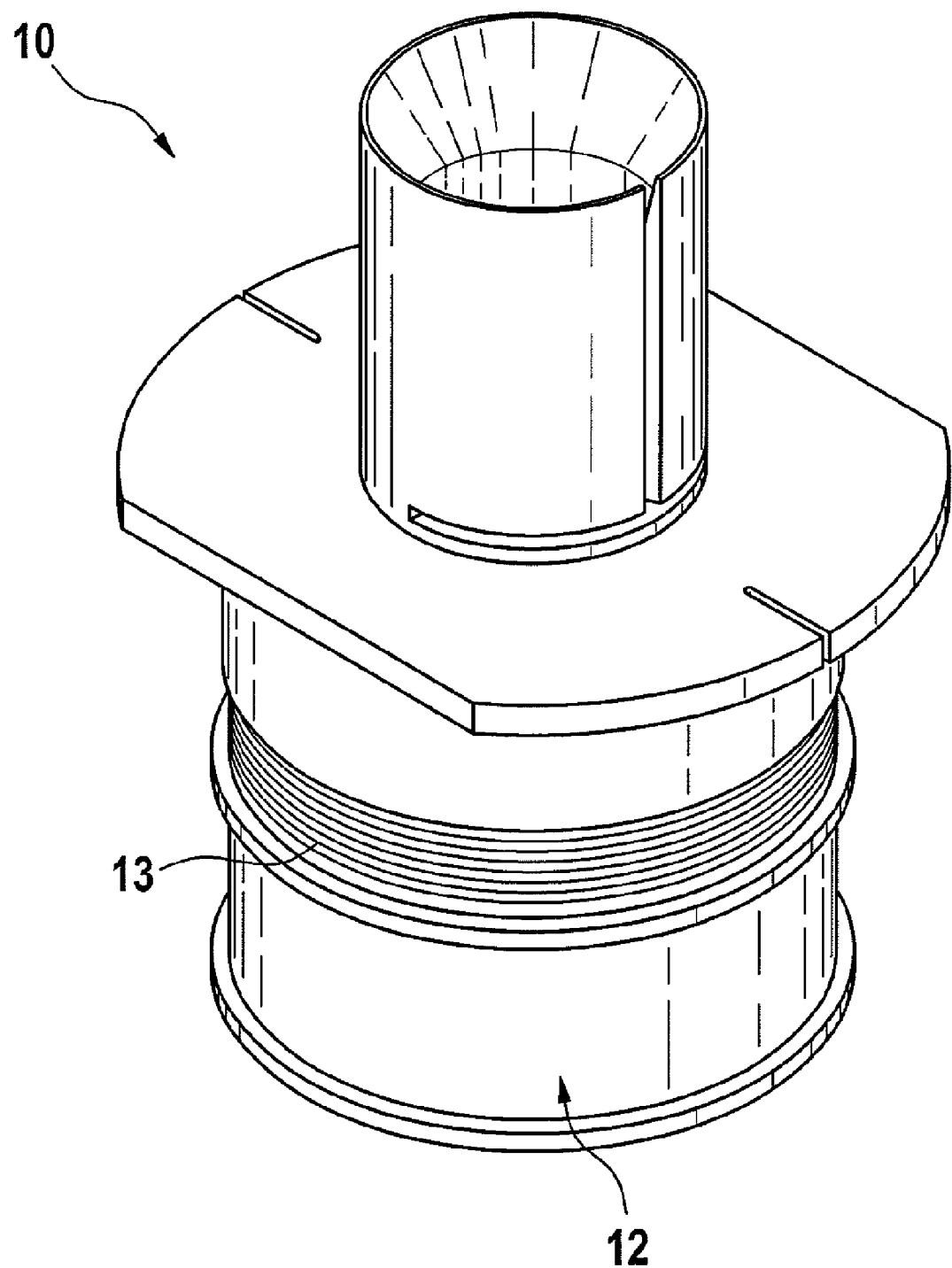
FIG. 2 is a perspective view of a coil body of a puncture element drive of the device shown in FIG. 1.
Figure 3:
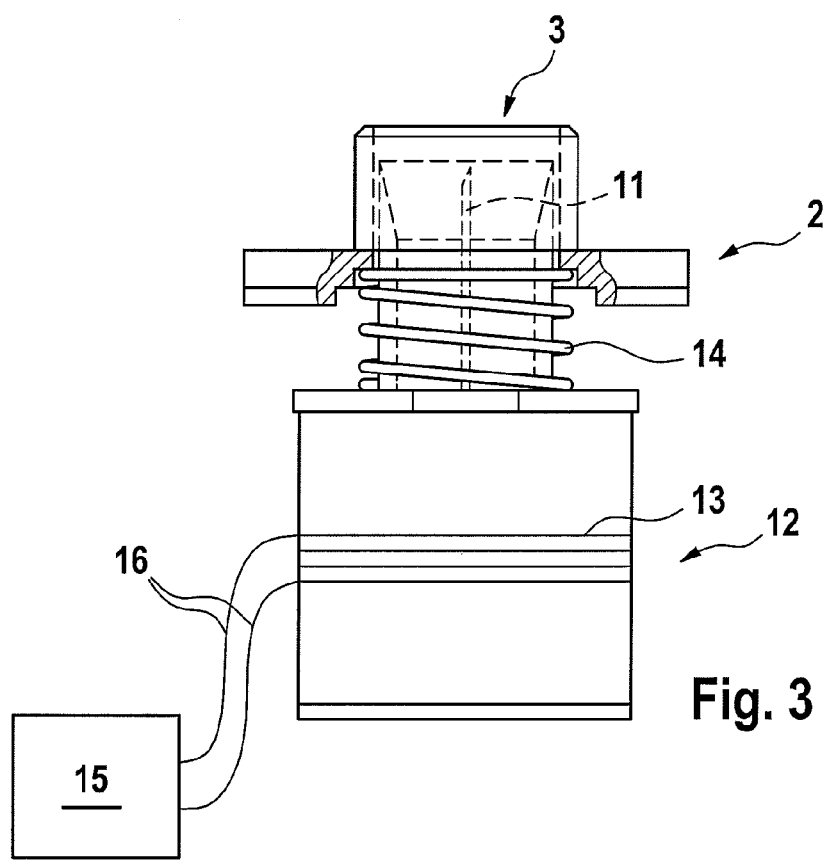
FIG. 3 is a side view of the drive of the device shown in FIG. 1.

The handheld apparatus 1 has a drive 10, the essential components of which are shown in FIGS. 2 and 3 and by which the puncture element 11 shown in FIG. 3 is movable in the direction towards the skin and in the direction away from the skin. The drive 10 can be an electromagnetic drive, such as described in U.S. Pat. No. 6,364,889, which is incorporated herein by reference with regard to the design of the drive.

The drive 10 comprises a coil body 12 made of plastic and carrying a coil 13. The coil body 12 is surrounded by a stationary magnetic case (not shown).

When an electric current flows through the coil 13, a magnetic force is generated. The direction and intensity of the magnetic force depends on the direction and intensity of the electric current. Depending on the direction of the magnetic force, the coil body 12 is pushed out of the magnetic case, i.e., forward for a puncture movement, or retracted for a return movement. To control the current intensity and thus the movement of the puncture element 11, a control unit 15 is used which provides a microprocessor control and is connected by connecting lines 16 to the coil 13.

As shown in FIG. 3, the coil body 12 carries a puncture element 11 in the form of a lancet. A compression spring 14 is arranged between the coil body 12 and the housing 2, whereby the puncture element 11 protrudes out of the device opening 3 only when there is a magnetic force driving the coil body 12 forward due to a corresponding coil current. When the coil body 12 is pushed forward, this causes compression of the spring 14 and a corresponding restoring force.

To obtain a sample of body fluid from a finger placed on the housing opening 3, the puncture element 11 is in a skin-opening step shifted forwardly so far that the tip of the puncture element penetrates into the epidermis but no blood-carrying tissue layers are reached. For most people, a depth of penetration of approximately 0.8 mm to 1.2 mm is optimal for this purpose. The coil current required for a corresponding lancet stroke is controlled by the control unit 15.

After the skin-opening puncture, the direction of current flow is reversed, so that the coil body 12 is retracted. The direction of the current is then reversed again, so that for the sample collection puncture, the coil body 12 is again accelerated in the direction towards the body part which is in contact with the opening 3 and penetrates into the skin. For the situation described here, namely, when the puncture element is stopped at the end of the sample collection step, the time interval between the end of the skin-opening step and the beginning of the sample collection step is preferably 1 msec to 1 sec, more preferably 1 msec to 30 msec. The end of the skin-opening step is defined by the stopping of the puncture element in the skin-opening puncture. The start of the sample collection step is defined by the re-acceleration of the puncture element for the sample collection puncture. Between the end of the skin-opening step and the beginning of the sample collection step, the puncture element can be retracted and can be withdrawn completely out of the epidermis.

In the skin-opening puncture, the skin surface at the puncture site is indented because the stratum corneum due to its strength resists puncture by the puncture element 11. In the subsequent sample collection step, this effect of indentation no longer occurs or occurs to a much smaller degree. Therefore, in the sample collection step, a greater puncture depth is reached even if the movement stroke of the puncture element is unchanged in relation to the opening 3 with which the body part is in contact. Therefore, if the stroke of the puncture element in the sample collection step is the same, the skin opening is typically deepened by approximately 100 µm to 500 µm, preferably 100 µm to 300 µm.

The puncture element may, in exemplary embodiments, be provided as a microneedle with which a small amount of blood is withdrawn by means of capillary action from the puncture wound created thereby. To optimize the collection of blood, it is advantageous to retract the puncture element after the blood collection puncture by a portion of the puncture distance into a collection position and to leave it there for a collecting period of a few seconds, for example. Thereby, a portion of the puncture channel is free for collecting body fluid therein and the body fluid can penetrate from there into a capillary structure of the puncture element.

Figure 4:
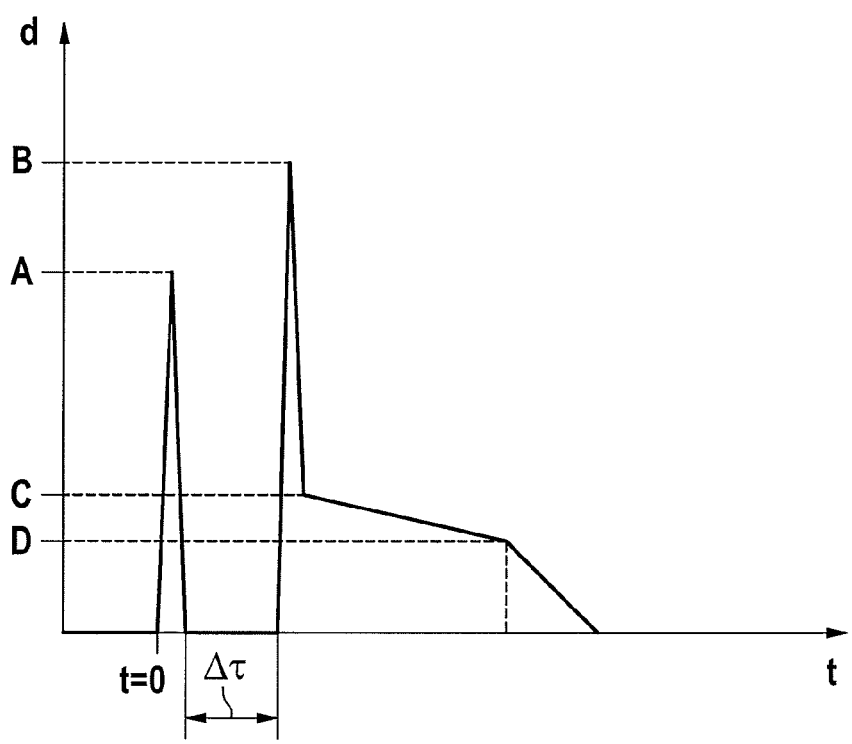
FIG. 4 is a graph illustrating a puncture profile according to an embodiment of the present invention.

FIG. 4 shows an example of a puncture profile comprising a skin-opening puncture, a sample collection puncture and a subsequent collection phase. The puncture depth "d" of the puncture element is plotted as a function of time. FIG. 4 shows that the puncture element first penetrates in the skin-opening puncture to a puncture depth A. Then the puncture element is retracted completely out of the skin with a return movement. After a period of time $\Delta\tau$, the sample collection puncture is performed, during which the puncture element is again inserted into the skin opening created before, and the skin opening is deepened to the puncture depth B.

Then the puncture element is retracted by a return movement into a collection position in which it protrudes into the skin only to a depth C. When approaching the collection position, the puncture element is decelerated. During a subsequent collection phase of typically 1 sec to 3 second duration, the puncture element is retracted slowly to a depth D. During the collection phase, blood is collected from the puncture wound via a capillary channel in the puncture element. After termination of the collection phase, i.e., on reaching the depth D, the puncture element is withdrawn completely from the puncture wound.

Figure 5:
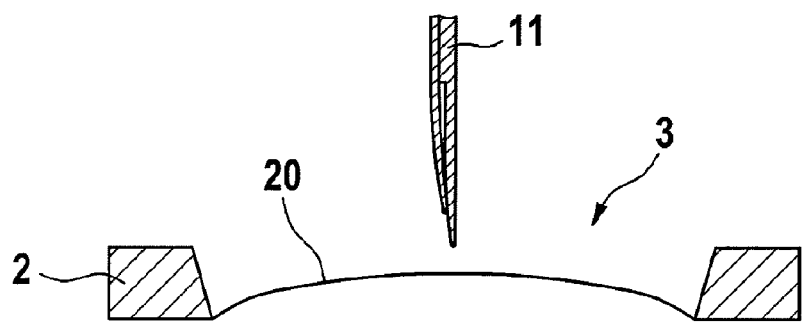
FIG. 5 is a schematic sectional view of an opening of the apparatus with a skin surface area adjacent thereto.

FIG. 5 shows the geometric relationships when a body part having a skin surface 20 is placed against the device opening 3. When the skin is pressed against the opening 3, its surface 20 bulges into the opening. This results in increased circulation at the puncture site and therefore facilitates sample collection. On the other hand, due to the curvature of the skin surface 20, precise reproducibility of the puncture depth is made difficult. Therefore, preferably, before the skin-opening puncture, the position of the skin surface 20 at the puncture site is determined in relation to a fixed reference point on the handheld apparatus, e.g., the housing 2 at the edge of the opening 3. This may be accomplished, for example, by an optical measurement or by an electrical measurement, e.g., an impedance measurement or a capacitive measurement in which the puncture element 11 is used as an electrode and is brought up to the skin surface 20 and then is retracted again to prepare for the skin-opening puncture.

Figure 7:
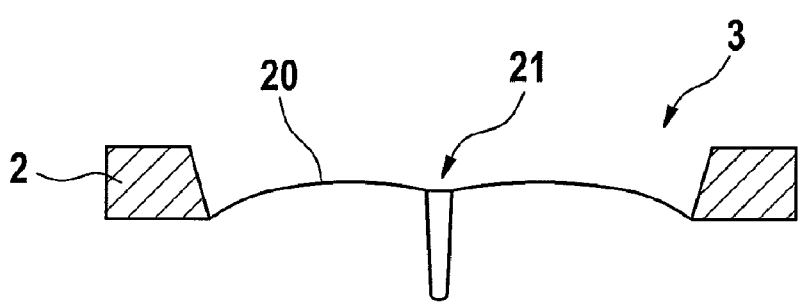
FIG. 7 is a view according to FIG. 5 with a skin opening created in the skin surface.

In the skin-opening puncture, the stratum corneum presents a significant resistance to the puncture element 11. FIG. 7 shows the resulting indentation (dimple) 22 produced in the skin surface 20 at the puncture site. After the skin-opening puncture, the puncture element 11 is retracted again, so that the skin surface 20 can relax into a resting position as shown in FIG. 7. This resting position is not identical to the starting position illustrated in FIG. 5 because of the change in the elastic properties of the skin surface 20 caused by the skin opening 21. However, it has been found in the context of these teachings that any differences occur with such a good reproducibly that a measurement of the position of the skin surface 20 is not necessary when creating the puncture wound. Rather, a precisely reproducible puncture depth can be ensured by detecting the position of the skin surface 20 before the skin-opening step.

Figure 6:
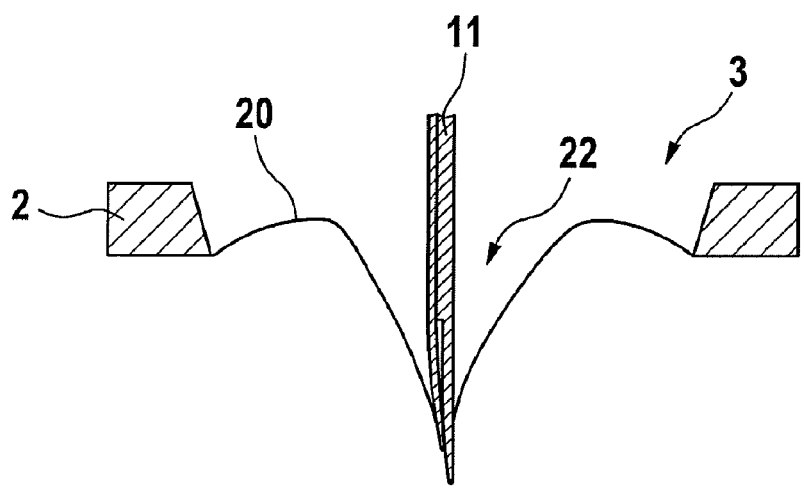
FIG. 6 is a view according to FIG. 5 during a skin-opening puncture.
Figure 8:
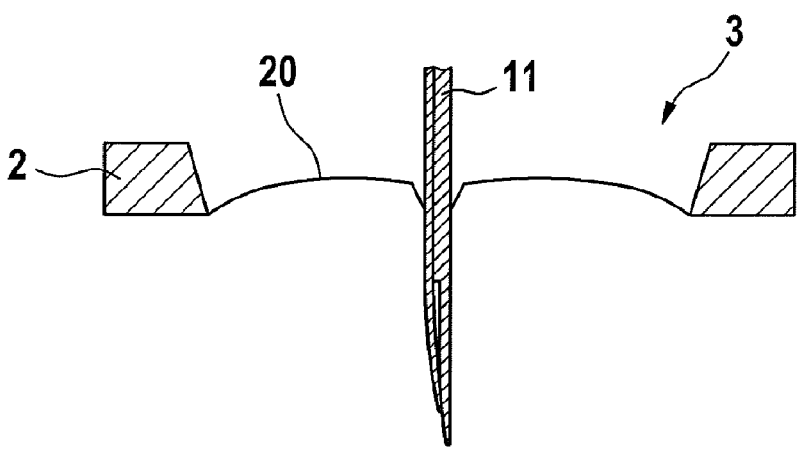
FIG. 8 is a view according to FIG. 5 showing the depth of the skin opening being increased to create a puncture wound.

The skin opening 21 illustrated in FIG. 7 is deepened with the sample collection puncture depicted in FIG. 8 to such an extent that blood-carrying tissue is reached. As FIG. 8 shows, the depth of the skin opening 20 can now be increased without the effect of indentation of the skin surface 20 (such as that illustrated in FIG. 6), occurring to a significant extent.

The embodiment described here is suitable in particular for handheld devices having a relatively large opening 3 with a diameter of at least 3 mm, preferably at least 5 mm. Even if a skin bulge occurs to a substantial extent, these teachings allow one to achieve a precisely reproducible puncture and consequently to obtain the advantages of easier sample collection due to better circulation in the puncture site.

A mechanical drive may be used instead of the electromagnetic drive illustrated in FIGS. 2 and 3. It may comprise a drive spring for generating a drive force and a drive rotor that executes a rotational movement, driven by the drive force. The control unit of such a handheld apparatus comprises a curve control, which is linked to the drive rotor and by means of which the rotational movements of the drive rotor are converted into movements of the puncture element in the direction towards the skin and in the direction away from the skin.

Figure 10:
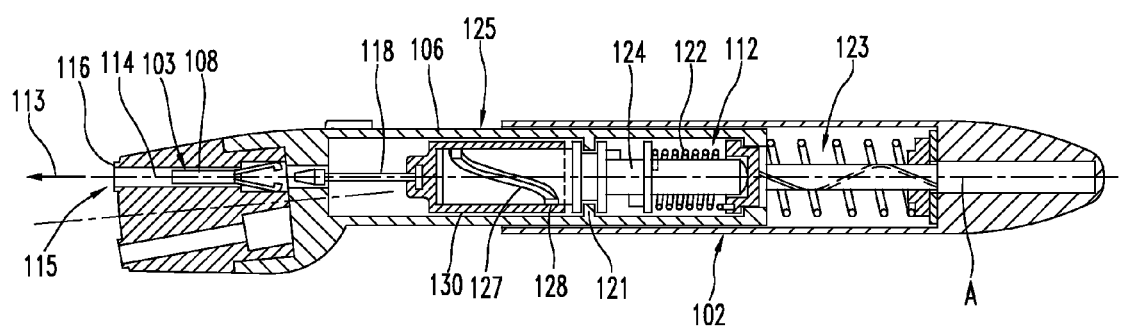
FIG. 10 is a side view of a longitudinal section of a blood removal system according to the present invention.

Such a mechanical drive is known from U.S. Pat. No. 7,223,276 and is also shown in FIG. 10. Referring to FIG. 10, in the housing 106 of the puncture apparatus 102, a lancet drive 112 is provided, which serves to move a lancet 103 with high speed in the puncturing direction 113, until its tip 114 protrudes from an exit opening 115, while the puncture apparatus 102 is pressed with a contact surface 116 surrounding the exit opening 115 against a body part (not shown). Thereby, a wound for removal of blood is produced in the body part. Before the puncturing movement is initiated, a respective lancet 103 must be coupled with the lancet drive 112. In the shown embodiment this is achieved by means of a connecting rod, designated as a pushrod 118.

The lancet drive 112 comprises essentially a drive spring 122, a cocking device 123 for tensioning of the drive spring 122, and a drive rotor 124 that is driven by the drive spring 122 and is rotatable about axis A. The drive rotor 124 is secured against axial displacement by means of a bearing pin 121. By means of an output-side coupling mechanism 125, the rotational movement of the drive rotor 124 is converted into the puncturing movement which is by means of the pushrod 118 transferred to a lancet coupled thereon.

The output-side coupling mechanism 125 is in the device of FIG. 10 embodied as a curve controller with a control curve 127 and a control pin 128 travelling along the control curve 127 during the puncturing movement. In the shown embodiment, the control curve 127 is formed by a recess running about the periphery of the drive rotor 124. The control pin 128 is formed on a driving sleeve 130, which surrounds the part of the drive rotor 124 provided with the control curve 127. The driving sleeve 130 is non-rotatably guided by means of a longitudinal groove (not shown), such that it can only carry out a translation movement. At its front end, the pushrod 118 is rigidly fixed.

The known device shown in FIG. 10 can be modified so that in a skin-opening step a skin opening is created at a puncture site in the epidermis and then, in a sample collection step, a sample collection puncture is performed in which the skin opening is deepened with the puncture element, thereby creating a puncture wound for collecting the sample. To this end, it is sufficient to modify the curve control in such a way that it has a shape with a first maximum for creating the skin opening and a second maximum for creating the puncture wound. With a suitably modified arrangement of the curve in the apparatus it is alternatively possible to use a control curve having two minimums.

Figure 9:
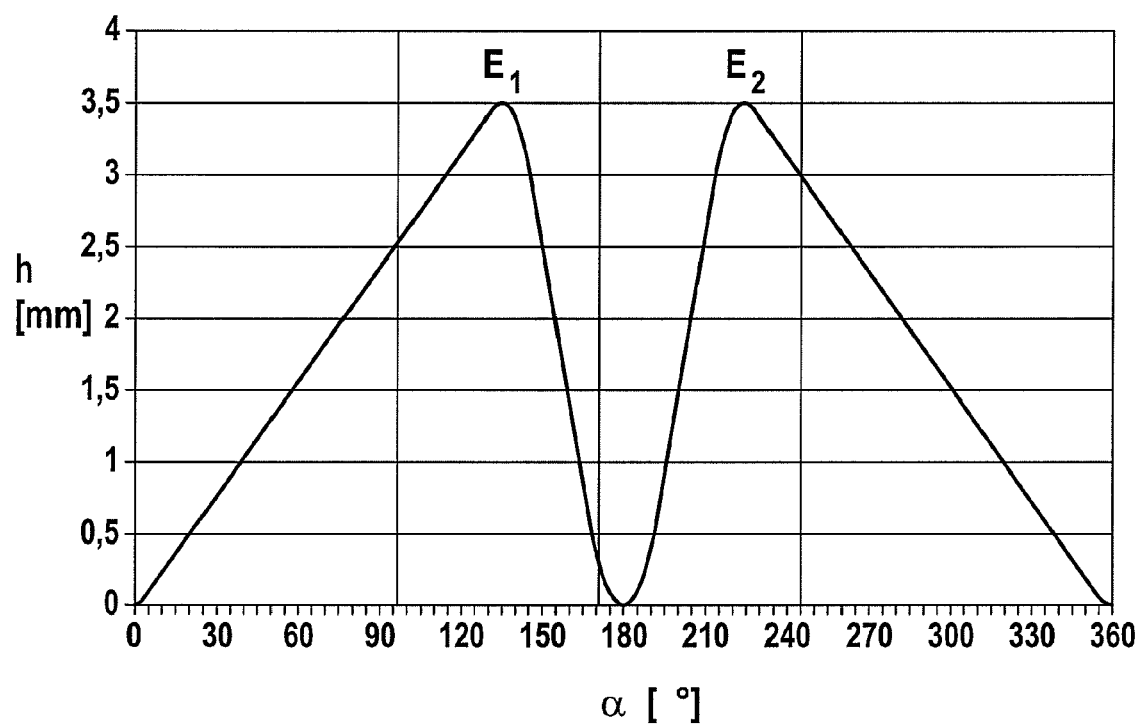
FIG. 9 depicts a control curve of a handheld apparatus having a rotor drive.

A schematic diagram of a suitable control curve, which may, for example, be embodied as a groove in the drive rotor, is shown in FIG. 9. This drive differs from that of the handheld apparatus described in U.S. Pat. No. 7,223,276 and shown in FIG. 10 essentially only in the shape of the control curve. With regard to the mechanical details of a suitable construction, reference is therefore made to U.S. Pat. No. 7,223,276, which is in this respect incorporated by reference herein. It is especially advantageous to provide an electric motor for tensioning the drive spring in the device. This electric motor may additionally assume other functions but is preferably used only for cocking the drive spring. Commercial batteries, rechargeable cells or even solar cells may be used to supply power to the electric motor, allowing a power supply that is independent of the power supply of the device.

FIG. 9 shows the lancet stroke "h" plotted as a function of the angle of rotation position α of the drive rotor in degrees. In the exemplary embodiment shown here, the lancet strokes h in the skin-opening puncture and in the sample collection puncture are each determined by an extremum $E_1$ and $E_2$, respectively, of the control curve. In the case shown it is the same for both punctures. Nevertheless, as already mentioned, a greater puncture depth is achieved in the sample collection puncture because the skin is noticeably indented in the skin-opening step and this effect of indentation does not occur at all, or only to a much lesser degree, in the sample collection puncture.

The control curve shown in FIG. 9 comprises an angle of rotation of the drive rotor of 360°. However, longer control curves of more than 360°, e.g., 540° are also possible. For more complex movement sequences, e.g., the described collection phase, it may be advantageous if the relaxation of the drive spring drives a rotational movement of the drive rotor of more than 360°, e.g., 540° and consequently the control curve traveler of the curve control travels an angle of rotation of the control curve of more than 360°, e.g., 540°.

The control curve used here may be a closed control curve according to FIG. 9, so that during tensioning and relaxation of the drive spring it is passed in one direction only. However, it is also possible to use an open control curve, i.e., a control curve with two ends at a distance from one another, so that the drive rotor rotates in a first direction of rotation during relaxation of the drive spring and the drive rotor rotates in a second direction of rotation for applying tension to the drive spring, the second direction of rotation being opposite to the first direction of rotation.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A handheld apparatus for creating a puncture wound in a body part having a layer of skin with an epidermis, the apparatus comprising:
   a puncture element;
   a drive for moving the puncture element toward and away from the skin;
   a housing adapted to contact a body part and having an opening by which the puncture element can puncture the body part;
   a control unit configured to automatically control movement of the puncture element, the control unit configured to automatically:
      move the puncture element in a skin opening step a first distance toward the skin with the drive, whereby a skin opening may be created;
      completely withdraw the puncture element from the body part at the end of the skin opening step; and then
      move the puncture element with the drive in a sample collection step toward the skin a second distance that is as great or greater than the first distance, whereby a puncture wound for collecting a sample may be created;
   wherein, the movement of the puncture element in the skin opening step and the movement of the puncture element in the sample collection step comprise consecutive movements;
      further wherein, the time interval between the time at which the puncture element is completely withdrawn from the body part at the end of the skin opening step and the time at which the puncture element first enters the body part during the sample collection step is 1 millisecond to 1 second, to thereby allow the epidermis at the skin opening to relax.

2. The apparatus of claim 1, wherein the control unit is operable to retract the puncture element before the step of moving the puncture element toward the skin the second distance.

3. The apparatus of claim 1, wherein:
   the drive comprises a drive spring for generating a drive force and a drive rotor that is rotatingly driven by the drive force during operation of the apparatus;
   the control unit comprising a curve control linked to the drive rotor; and
   rotational movements of the drive rotor are converted through the control curve into movements of the puncture element toward and away from the skin.

4. The apparatus of claim 3, wherein the curve control comprises a control curve traveler which travels along a control curve of the drive rotor during a rotational movement of the drive rotor.

5. The apparatus of claim 4, wherein the control curve has a shape comprising a first extremum corresponding to the first distance and a second extremum corresponding to the second distance.

6. The apparatus of claim 4, wherein the control curve comprises an angle of rotation of the drive rotor of at least 360°.

7. The apparatus of claim 4, wherein relaxing the spring results in a rotational movement of the drive rotor of more than 360°.

8. The apparatus of claim 4, wherein the control curve is an open control curve.

9. The apparatus of claim 4, wherein, during relaxation of the drive spring, the drive rotor turns in a first direction of rotation and the drive spring is tensioned by the drive rotor when the drive rotor turns in a second direction of rotation, the second direction of rotation being opposite the first direction of rotation.

10. The apparatus of claim 1, further comprising a housing having a housing opening with a pressure ring for contacting to a body part in which a puncture wound is to be created, the puncture element being extendable through the pressure ring.

11. The apparatus of claim 1, wherein the lancet strokes resulting from moving the puncture element the first distance and the second distance are substantially the same.

12. The apparatus of claim 1, wherein the second distance is greater than the first distance.

13. The apparatus of claim 1, wherein the time interval is 1 millisecond to 30 milliseconds.

14. The apparatus of claim 1, further comprising a device which is operable to determine the position of the surface of the epidermis relative to a fixed reference point on the apparatus.

15. The apparatus of claim 1, wherein the control unit is operable to retract the puncture element into a collection position in which the tip of the puncture element remains within the skin.

16. The apparatus of claim 15, wherein the control unit is operable to decelerate the puncture element as the puncture element approaches the collection position.

17. The apparatus of claim 1, wherein movement of the puncture element through the first distance creates a skin opening having a depth of 0.4 mm to 2.0 mm.

18. The apparatus of claim 17, wherein movement of the puncture element through the first distance creates a skin opening having a depth of 0.8 mm to 1.2 mm.

* * * * *